(12) United States Patent
Nord et al.

(10) Patent No.: US 8,121,252 B2
(45) Date of Patent: Feb. 21, 2012

(54) USE OF PLANNING ATLAS IN RADIATION THERAPY

(75) Inventors: Janne Nord, Espoo (FI); Corey Edmund Zankowski, San Jose, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 30 days.

(21) Appl. No.: 12/402,393

(22) Filed: Mar. 11, 2009

(65) Prior Publication Data

US 2010/0232572 A1 Sep. 16, 2010

(51) Int. Cl.
*A61N 5/10* (2006.01)
(52) U.S. Cl. .......................................... 378/65
(58) Field of Classification Search .............. 378/65
See application file for complete search history.

(56) References Cited

U.S. PATENT DOCUMENTS

| | | | | |
|---|---|---|---|---|
| 5,818,902 A * | 10/1998 | Yu | | 378/65 |
| 6,134,296 A * | 10/2000 | Siochi | | 378/65 |
| 6,314,159 B1 * | 11/2001 | Siochi | | 378/65 |
| 6,330,300 B1 * | 12/2001 | Siochi | | 378/65 |
| 6,349,129 B1 * | 2/2002 | Siochi | | 378/65 |
| 6,385,286 B1 * | 5/2002 | Fitchard et al. | | 378/65 |
| 6,477,229 B1 * | 11/2002 | Grosser | | 378/65 |
| 6,661,870 B2 * | 12/2003 | Kapatoes et al. | | 378/65 |
| 6,661,871 B2 * | 12/2003 | Siochi | | 378/65 |
| 6,687,330 B2 * | 2/2004 | Hernandez-Guerra | | 378/65 |
| 6,757,355 B1 * | 6/2004 | Siochi | | 378/65 |
| 6,813,336 B1 * | 11/2004 | Siochi | | 378/65 |
| 6,842,502 B2 * | 1/2005 | Jaffray et al. | | 378/65 |
| 6,853,705 B2 * | 2/2005 | Chang | | 378/65 |
| 6,907,282 B2 * | 6/2005 | Siochi | | 600/411 |
| 7,212,608 B2 * | 5/2007 | Nagamine et al. | | 378/65 |
| 7,343,030 B2 * | 3/2008 | Sawyer | | 382/128 |
| 7,362,848 B2 * | 4/2008 | Saracen et al. | | 378/65 |
| 7,609,809 B2 * | 10/2009 | Kapatoes et al. | | 378/65 |
| 7,623,679 B2 * | 11/2009 | West et al. | | 382/103 |
| 7,646,936 B2 * | 1/2010 | Nord et al. | | 382/294 |
| 7,668,292 B1 * | 2/2010 | Bose et al. | | 378/65 |
| 7,756,359 B1 * | 7/2010 | Nord et al. | | 382/294 |

* cited by examiner

*Primary Examiner* — Allen C. Ho
(74) *Attorney, Agent, or Firm* — Vista IP Law Group, LLP.

(57) ABSTRACT

A method for determining a radiation treatment plan for a patient includes determining a reference plan, the reference plan including information regarding a reference region that has a different configuration from that of a region in the patient, and using the reference plan to determine the treatment plan for the patient. A method for use in a treatment planning process includes determining a reference plan that includes information regarding a reference region, determining a deformation field that registers the reference region in the reference plan with a region for a patient, and determining a result of using the reference plan as it applies for the patient.

35 Claims, 7 Drawing Sheets

New patient 00000
01110
02220
01110
00000

FIG. 4A

Reference patient 1 (Good match)

Reference patient 2 (Bad match)

New patient image data 00000
01110
02220
01110
00000

Reference patient image data 01110
01110
02220
02220
01110
01110

Dose profile in reference patient 01210
01210
04540
04540
01210
01210

Deformed dose profile for new patient 00000
01210
04540
01210
00000

FIG. 5D

USE OF PLANNING ATLAS IN RADIATION THERAPY

FIELD

This application relates generally to radiation therapy, and more specifically, to systems and methods for determining and/or using a radiation treatment plan.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. During a radiation planning session, radiation treatment planning is performed before treatment radiation is delivered to a patient. This allows an accurate and precise dosage of radiation to be delivered to a patient.

In a typical radiotherapy treatment planning process, clinicians identify the target region (e.g., tumor) and critical organs from a three-dimensional image (e.g., CT image) of the patient, and manually segment the tumor (to receive a prescribed dose of radiation) and critical organs that are at risk of damage from the radiation treatment. Although there are guidelines that govern the entire planning process, each patient is different from the last, and therefore, each planning process is customized. The variability between patient anatomy, image quality, and tissue response to radiation means that it has not been possible to reliably automate the planning process, making treatment planning a time consuming process.

SUMMARY

In accordance with some embodiments, a method for determining a radiation treatment plan for a patient includes determining a reference plan, the reference plan including information regarding a reference region that has a different configuration from that of a region in the patient, and using the reference plan to determine the treatment plan for the patient. The reference region may include healthy tissue, unhealthy tissue (e.g., tumorous tissue), or both healthy and unhealthy tissue.

In accordance with other embodiments, a computer product includes a medium for storing a set of instructions, an execution of which causes a process for determining a radiation treatment plan for a patient to be performed, the process comprising determining a reference plan, the reference plan including information regarding a reference region that has a different configuration from that of a region in the patient, and using the reference plan to determine the treatment plan for the patient. The reference region may include healthy tissue, unhealthy tissue (e.g., tumorous tissue), or both healthy and unhealthy tissue.

In accordance with other embodiments, a system for determining a radiation treatment plan for a patient includes means for determining a reference plan, the reference plan including information regarding a reference region that has a different configuration from that of a region in the patient, and means for using the reference plan to determine the treatment plan for the patient. The reference region may include healthy tissue, unhealthy tissue (e.g., tumorous tissue), or both healthy and unhealthy tissue.

In accordance with other embodiments, a method for use in a treatment planning process includes determining a reference plan that includes information regarding a reference region, determining a deformation field that registers the reference region in the reference plan with a region for a patient, and determining a result of using the reference plan as it applies for the patient. The reference region may include healthy tissue, unhealthy tissue (e.g., tumorous tissue), or both healthy and unhealthy tissue.

In accordance with other embodiments, a computer product includes a medium for storing a set of instructions, an execution of which causes a process to be performed, the process comprising determining a reference plan that includes information regarding a reference region, determining a deformation field that registers the reference region in the reference plan with a region for a patient, and determining a result of using the reference plan as it applies for the patient. The reference region may include healthy tissue, unhealthy tissue (e.g., tumorous tissue), or both healthy and unhealthy tissue.

In accordance with other embodiments, a system for use in a treatment planning process includes means for determining a reference plan that includes information regarding a reference region, means for determining a deformation field that registers the reference region in the reference plan with a region for a patient, and means for determining a result of using the reference plan as it applies for the patient. The reference region may include healthy tissue, unhealthy tissue (e.g., tumorous tissue), or both healthy and unhealthy tissue.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIGS. 4A-4C illustrate representations of a target region for a patient, a first reference target region, and a second reference target region, respectively;

FIGS. 5A-5D illustrate a concept of deforming a reference dose distribution in accordance with some embodiments;

DESCRIPTION OF THE EMBODIMENTS

Figure 1:
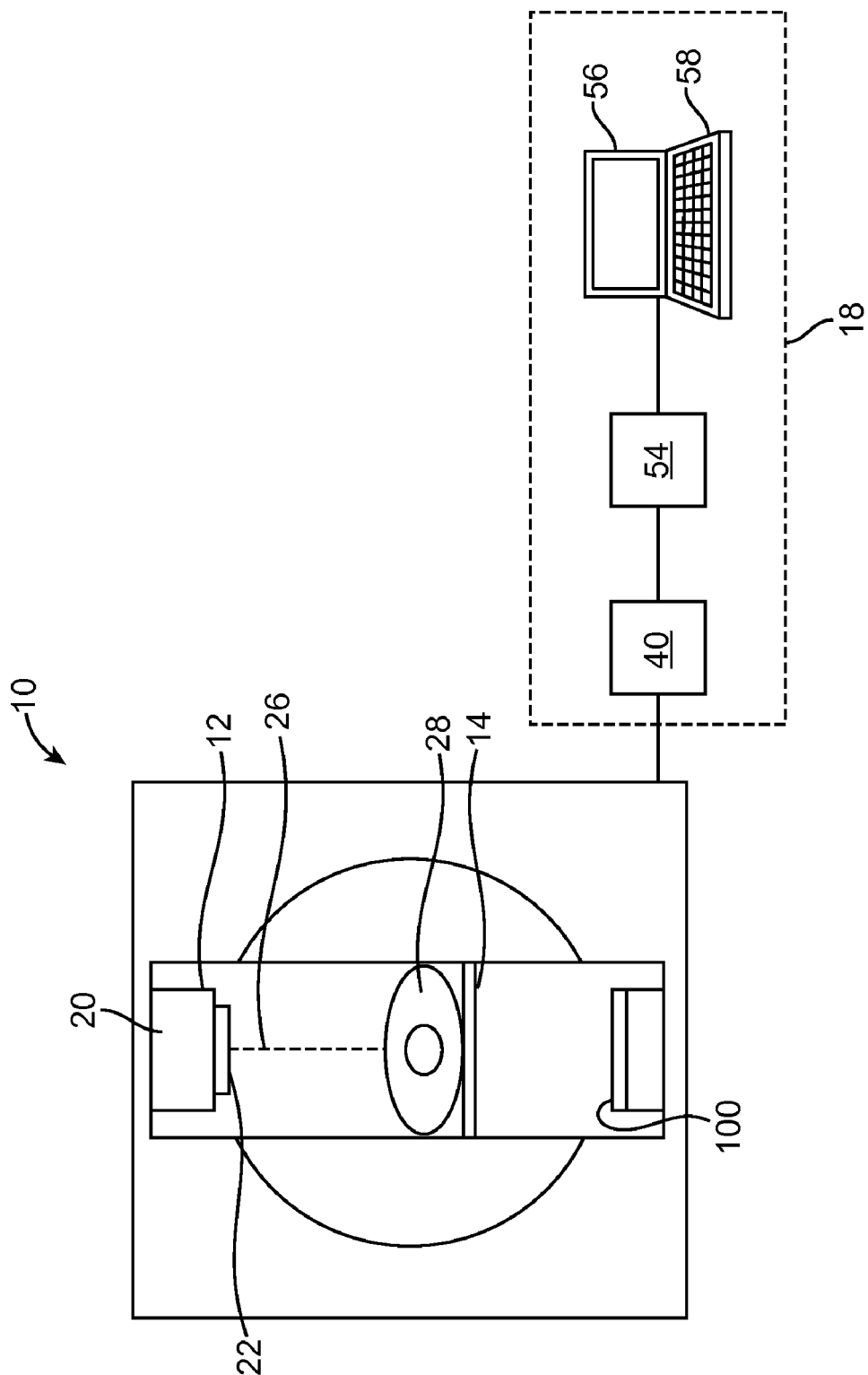
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

In accordance with some embodiments, new patient image (s) is compared to previous patient images from a library of reference files (ATLAS) to find one or more candidates that closely match the anatomy of the new patient. Deformable image registration techniques are used to morph anatomy images from the library so that they match that of the new patient. Optionally, the knowledge contained in the ATLAS, such as treatment techniques, organ delineation, as well as the approved dose distributions, may be applied to the new patient's treatment plan and incorporated into a treatment plan optimization process to automatically establish a first approximation of an optimized treatment plan for the new patient. In some embodiments, during the optimization process to determine the new treatment plan using information from the library, rather than, or in addition to, collapsing the dose distribution into 2D DVHs, the 3D nature of the dose distribution is preserved.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, now U.S. Pat. No. 6,888,919, and U.S. patent application Ser. No. 10/687,573, entitled "MULTI-ENERGY X-RAY SOURCE," filed on Oct. 15, 2003, now U.S. Pat. No. 7,649,981. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 28, and during a treatment procedure, the gantry 12 rotates about the patient 28 (as in an arch-therapy). In other embodiments, the gantry 12 does not rotate about the patient 28 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. In addition, in other embodiments, the gantry 12 may be tiltable about one or more axes. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient. Thus, as used in this specification, the term "radiation" is not limited to x-ray, and may refer to a particle beam, such as a proton beam.

Figure 2:
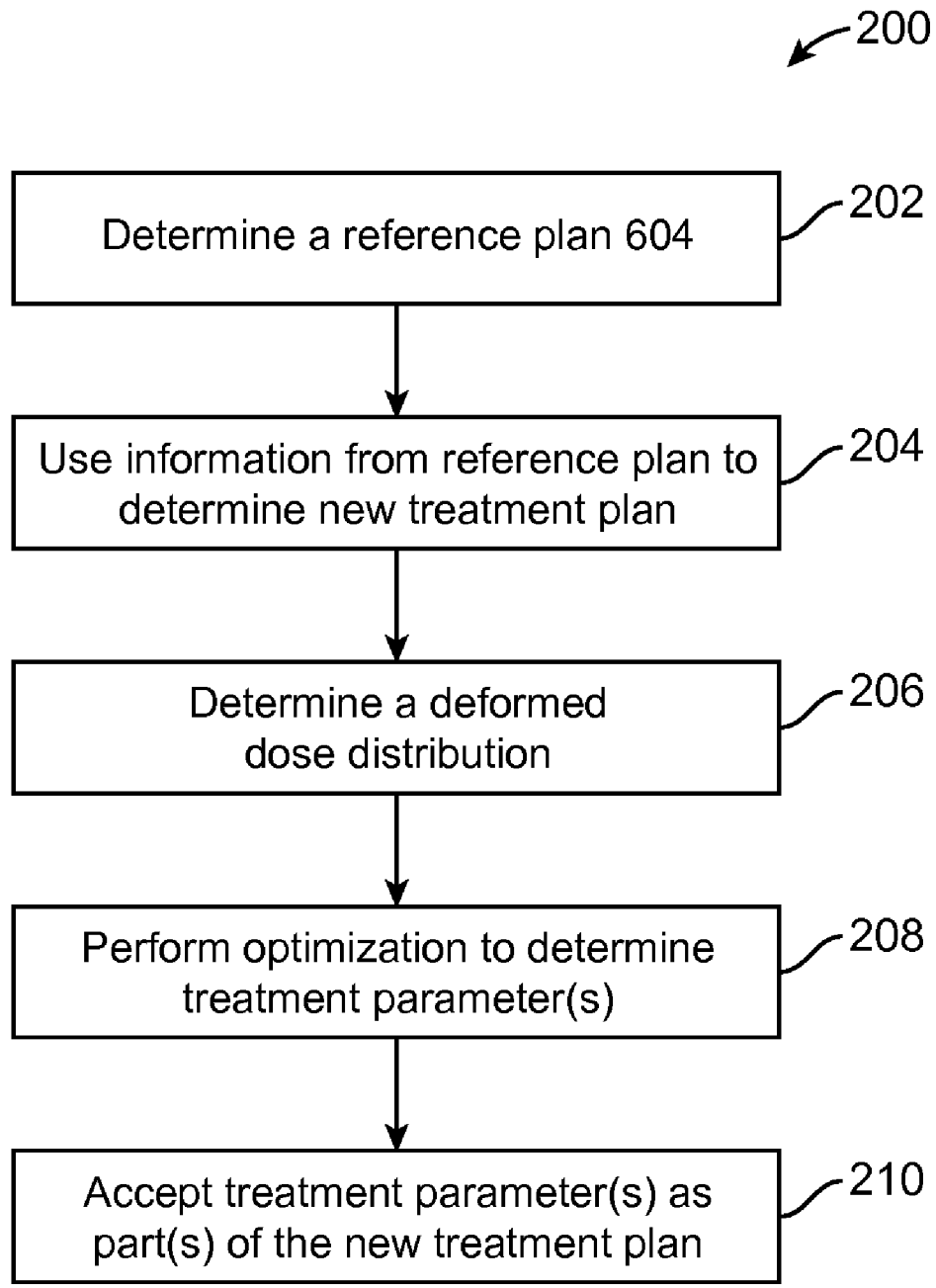
FIG. 2 illustrates a method for use in a method to determine a treatment plan in accordance with some embodiments.
Figure 3:
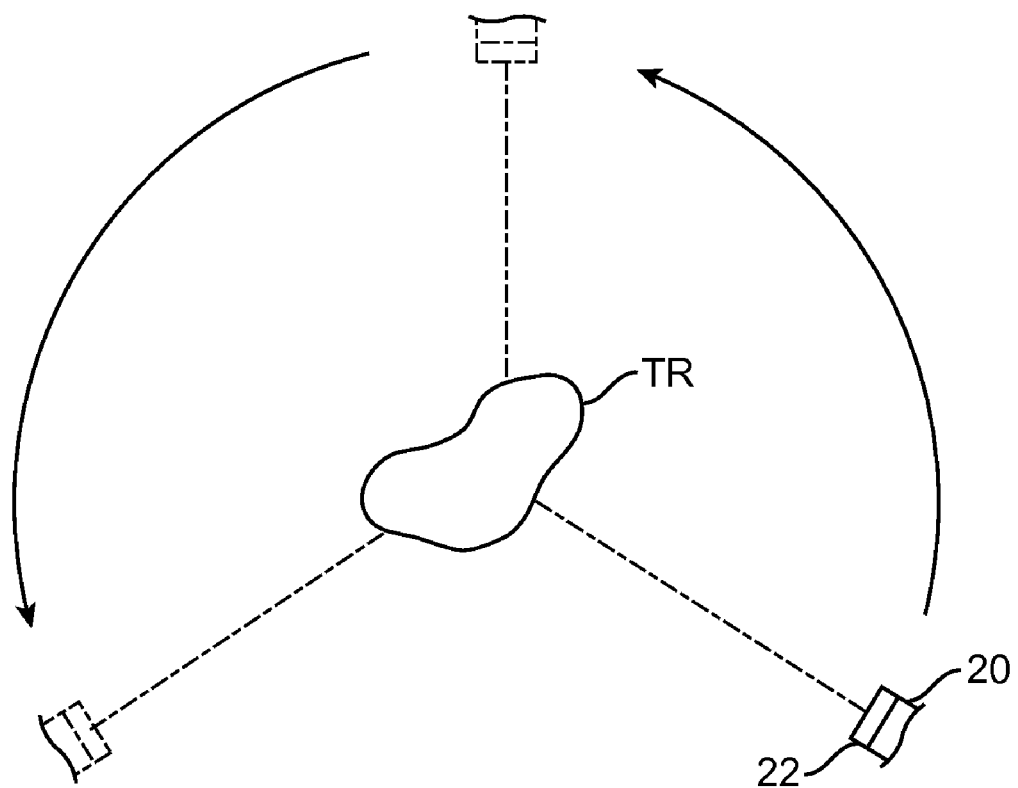
FIG. 3 illustrates an example of a target region being treated using a radiation source that rotates about the target region.

FIGS. 2-6 illustrate a method 200 of determining a radiation treatment plan that may be used by the system 10 in accordance with some embodiments. The method 200 will be described with reference to treating a target region TR using a radiation source 20 that rotates about the target region TR (e.g., 360° or less about the target region TR), as in an arc therapy (FIG. 3). However, it should be understood that the method 200 is not limited to the example illustrated in FIG. 3, and that the method 200 may be used to determine other treatment plans with a different setup. For example, in other embodiments, the method 200 may be used to determine a treatment plan in which the radiation source 20 and the target region TR translate relative to each other, such as by movement of the patient support 14. Such may be performed in the alternative, or in addition to, rotating the source 20 relative to the target region TR. It should be noted that the term "target region" as used in this specification is not limited to only tumorous tissue or tissue with undesirable condition, and may be used to refer to healthy tissue, such as healthy tissue outside tumorous tissue and within a margin from the tumorous tissue.

Figure 6:
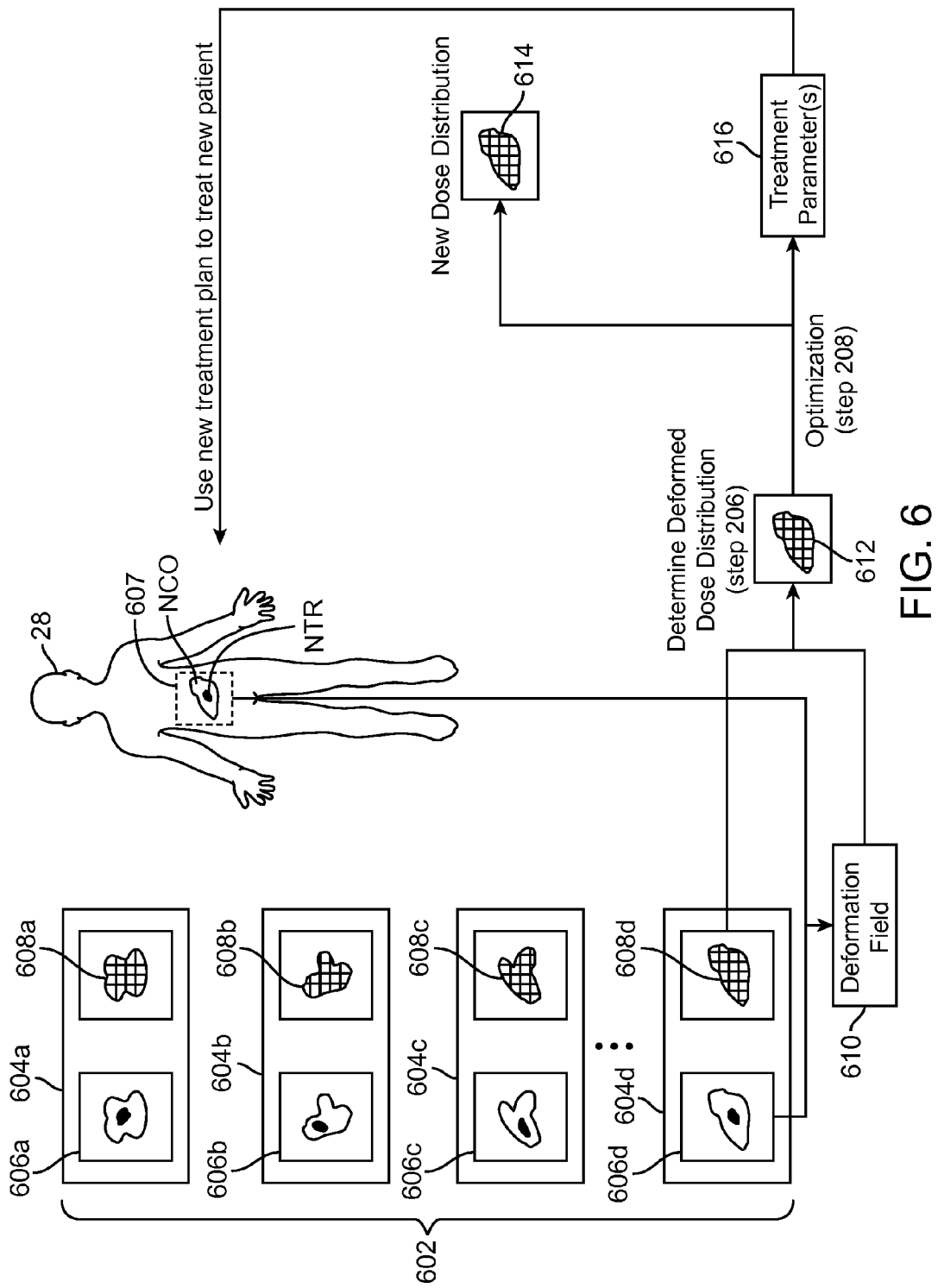
FIG. 6 is a flow diagram illustrating the components involved in the method of FIG. 2.

First, a reference plan 604 is determined (step 202). A reference plan is a plan or a collection of data that includes information regarding a treatment. In the illustrated embodiments, the reference plan is automatically determined using a processor (e.g., the processor 54) based on a case classification. In some embodiments, there may be different reference plans 604 for treating different organs, respectively. For example, there may be one or more reference plans for lung, one or more reference plans for liver, one or more reference plans for head and neck, etc. If the treatment plan is for treating a prostate for the new patient, then the processor 54 is configured to automatically select, from a collection 602 of reference plans 604 (ATLAS), a reference plan 604 for prostate treatment based on an input from a user (e.g., an input identifying that it is the prostate that is desired to be treated in the new patient) (FIG. 6). In other embodiments, the reference plan 604 may be determined based on case classification (s) that are more detailed. For example, there may be a reference plan 604 for young patient with head and neck cancer, and another reference plan 604 for old patient with head and neck cancer. In such cases, the processor 54 is configured to automatically select a reference plan 604 based on a match of the organ type and patient age. Thus, the case classification for the selection of a reference plan 604 may be based on one or a combination of a patient's weight, a patient's age, a patient's height, a patient's sex, an organ to be treated, an organ's size, an organ's shape, a medical condition (e.g., diagnosis, stage, grade information for a cancerous disease, etc.), and a medical history. In some cases, medical history information may be important in planning for radiation treatment because past radiation treatments may limit the allowable dose in a subsequent treatment due to normal tissue tolerances, for example. In other embodiments, the determination of the reference plan 604 may be performed by a user, who selects a reference plan 604 from among a plurality of reference plans 604. In such cases, a computer user interface (e.g., the monitor 56) may be provided, which displays graphics for allowing the user to select the reference plan 604. In some embodiments, the reference plan 604 can be derived at least in part from anatomical atlas information. The reference plan 604 can also be derived or adopted at least in part from plans already defined and/or reviewed by medical experts.

In other embodiments, the determination of the reference plan 604 may be performed based on a match between an image 606 from the reference plan 604 and an image 607 of the new patient 28 (FIG. 6). In some embodiments, the image 606 from the reference plan 604 and the new patient image 607 may be CT/volumetric images. In other embodiments, the reference plan image 606 and the new patient image 607 may be other types of images, such as MRI images, ultrasound images, x-ray images, PET images, SPECT images, etc. Also, in further embodiments, the image 606 from the reference plan 604 may be created using a different imaging modality from that for the new patient image 607. For example, the reference plan image 606 may be a portion of a CT image, while the new patient image 607 may be a MRI image.

In some embodiments, the processor 54 may determine a set of reference plans 604 that are possible candidates for the new patient 28. For example, based on the criteria that the new treatment is for treating a lung, and the height of the new patient 28, the processor 54 may select from the library 602 a set of reference plans 604 (e.g., 604a-604d) that fit the criteria (FIG. 6). In such cases, the processor 54 then perform further analysis to determine which of the reference plans 604 is the best match for the new patient 28. In the illustrated embodiments, the matching between an image 606 (e.g., one of 606a-606d) from the reference plan 604 and an image 607 of the new patient 28 may be performed based on deformable image registration. Deformable image registration is a process or technique in which points in a first image of a first object (such as a reference target region RTR and/or a reference critical organ RCO) are associated with corresponding points in a second image of a second object (such as a new target region NTR and/or a new critical organ NCO), wherein the first and second objects may have different sizes and/or shapes.

FIGS. 4A-4C illustrate such concept. FIG. 4A illustrates a representation (which may be an image or a modeling) of a region in the new patient 28 in which value 0 represents air outside the patient, 1 represents a healthy tissue, and 2 represents tumorous tissue. FIG. 4B illustrates a representation (which may be a reference image or a reference modeling) of a region from a first reference plan 604 (e.g., for reference patient 1), and FIG. 4C illustrates another representation of a region from a second reference plan 604 (e.g., for reference patient 2). In the illustrated example, deformable registration could be performed between the new patient 28 and the reference patient 1, and another deformable registration could be performed between the new patient 28 and the reference patient 2. In the example, the deformation field resulted from the deformable registration between the new patient 28 and the reference patient 1 is a scaling field. On the other hand, the deformation field resulted from the deformation registration between the new patient 28 and the reference patient 2 is more complex, because the reference patient 2 image cannot simply be translated, rotated, and/or scaled to achieve the new patient image. Thus, in the above example, since the patient 1's reference image can be more easily morphed to match the new patient image, the patient 1's reference image is better than the patient 2's reference image for use to determine the new treatment plan for the new patient 28. In other embodiments, the deformable registration may utilize image of the patient that does not include tumorous tissue. For example, in other embodiments, the value "2" in the above example may represent healthy tissue (i.e., instead of tumorous tissue) with a characteristic that is different from that of the healthy tissue represented by the value "1."

In the illustrated embodiments, the processor 54 is configured to compare the new patient image 607 with reference images 606 from different reference plans 604, and select one of the reference plans 604 based on a best match. In some embodiments, the processor 54 may be configured to determine a score that represents how well each deformation field (for each reference plan 604) could be represented by a common (i.e., same for a set of points in the image) translation, a common rotation, a common scaling, or a combination of any of the foregoing. In such cases, the processor 54 is configured to select the reference plan 604 with the best score. It should be noted that the image/modeling of the region of the patient 28 is not limited to a two dimensional matrix illustrated in the above examples shown in FIGS. 4A-4C, and that in other embodiments, the image/modeling may be a three dimensional matrix.

The deformation field 610 resulted from the deformation registration that maps points from the reference patient image 606 to the new patient image 607 may include a rigid component, such as a translation component, a rotation component, or a combination of both. For example, consider the following reference patient image 606 and new patient image 607:

01200133000 Reference patient image
00012001300 New patient image

The deformation field 610 that maps the reference patient image 606 to the new patient image 607 would be:

22222221111 in which each number denotes how much the corresponding point in the reference patient image 606 needs to be moved to the right in order to match the new patient image 607. In some embodiments, the rigid component(s) (e.g., translation component, rotation component) and/or the scaling component in the deformation field 610 may be removed to allow a user to evaluate how well a reference image 606 matches the new patient image 607. Using the above example, the rigid component may be removed from the deformation field 610 to obtain the remaining deformation field, as follow:

| | |
|---|---|
| 22222221111 | Deformation field |
| 22222222222 | Rigid component (shift image to right by two units) |
| 0000000(−1)(−1)(−1)(−1) | Remaining component in deformation field |

The rigid component and the remaining component of the deformation field 610 may be applied to the reference image 606 to accomplish the new patient image 607, as follow:
01200133000 Reference patient image
00012001330 Applying rigid component (shift image to right by two units)
00012001300 Applying remaining component (move latter part left by one unit)

As shown in the above example, the region that comprises of 3's is compressed to fit the new patient image 607. Thus, the deformation field 610 contains a rigid component that moves the reference image 606 to the right by two units, and a component that compresses the region with 3's.

In some embodiments, the processor 54 is configured to determine how much deformation is needed to achieve the new patient image 607 after the translation component(s), rotation component(s), and scaling component(s) are removed from the deformation filed 610. This would allow a user to know how much localized change in the reference image 606 is needed in order to achieve the new patient image 607. For example, in the above example, the processor 54 may calculate that there is one point in the image where compression occurs. In another embodiment, the processor 54 may calculate how much absolute movement is left in the remaining component in order to achieve the new patient image 607. In the above example, the processor 54 would determine that there are four components (with value of −1) in the remaining component that are needed to be adjusted in order to achieve the new patient image 607.

In some embodiments, the processor 54 is configured to determine different remaining deformation fields for different respective reference plans 604 that are potential candidates, and automatically select the reference plan 604 that has the least remaining deformation field. This is because the amount of deformations in region of interest (e.g., where there is tissue with constraint(s), such as healthy tissue or tumorous tissue) is an indirect measure of how much the dose distribution in the new patient 28 would change compared to the reference dose distribution from the reference plan 604. Thus, the remaining deformation field may provide some indication of how much the new dose distribution (to be determined using the corresponding reference plan 604) would deviate from the reference plan 604. For example, if the remaining deformation field indicates that a lot of changes are needed to map a reference image 606 to the new patient image 607, that may be an indication that the resulting new dose for the new patient 28 (determined using the corresponding reference plan 604) may deviate significantly from the reference plan 604. In such cases, the processor 54 may choose not to select such reference plan 604.

In some embodiments, the processor 54 may remove the rotation, translation, and scaling components from the deformation field 610 by finding the best combination of these components that would result in the smallest amount of change in the remaining deformation field. The processor 54 then selects the reference plan 604 that has the smallest amount of change in the remaining deformation field. For example, the translation component may be determined by calculating the average vector inside a region of interest. In some embodiments, the processor 54 may match the rotation-translation-scaling matrix to the deformation filed 610, and apply the inverse matrix operation of the rotation-translation-scaling matrix to the deformation. For example, the processor could find a rotation-translation-scaling matrix that best reproduces the deformation field (after applying the matrix operation to the deformation field the sum of lengths of deformation vectors is as small as possible).

In other embodiments, the processor 54 may be configured to calculate divergence and curl components of the deformation field 610 for each point, convert those to absolute values, and integrate over the field. The processor 54 then uses the result to select the reference plan 604. The above techniques provide information regarding how much different the relative positions of the biological reference points are in the images. They also provide information about where the differences are (e.g., locations where the deformation field is divergent).

It should be noted that the deformable registration technique that may be used is not limited to the examples described, and that other deformable registration techniques may be used in different embodiments. Deformable image registration algorithms are known in the art, and will not be described in further details. Also, it should be noted that any of the deformation field, the translation component(s), the rotation component(s), and the scaling component(s) is not limited to a two dimensional matrix illustrated in the above examples, and that in other embodiments, any of the deformation field, the translation component(s), the rotation component(s), and the scaling component(s) may be a three dimensional matrix, such as for the case in which a three dimensional reference image 606 is registered with a three dimensional image 607 for the new patient 28. Further, it should be noted that the remaining deformation field is not limited to having one localized change for an image, and that in other embodiments, the remaining deformation field may represent more than one localized changes in an image. For example, after the rigid component(s) and the scaling component(s) have been removed from the deformation filed 610, the remaining deformation field may indicate that a plurality of regions in the reference image 606 needs to be adjusted in order to fit the new patient image 607. One region may require compression, and another region may require expansion. In another case, one region may require compression by a first magnitude (e.g., 1 unit), and another region may require compression by a second magnitude (e.g., 3 units). Also, In some cases, the direction of compression/expansion in one region may be different from the direction of compression/expansion in another region.

Returning to FIG. 2, next, information from the reference plan 604 is transferred for use to determine the new treatment plan 616 (step 204). In the illustrated embodiments, the reference plan 604 contains information about how a specific patient (a reference patient) was previously treated. For example, the reference plan 604 may include data regarding one or more of a number of fields (e.g., IMRT fields), a field geometry/geometries (e.g., radiation entry direction(s)), the reference target region, a critical organ (e.g., image of a critical organ), a dose requirement (an objective for optimization), and a dose limit. The reference plan 604 may also include specific techniques for performing a certain treatment procedure. Any of these data may be used to determine the new treatment plan 616. In some embodiments, some or all of the information from the reference plan 604 are used to derive parameters for the new treatment plan 616. In other embodiments, some or all of the information from the reference plan 604 are used directly themselves as parameters for the new treatment plan 616. In further embodiments, some of the information from the reference plan 604 are used to derive parameters for the new treatment plan 616, and other information from the reference plan 604 are used directly themselves as parameters for the new treatment plan 616.

To illustrate, consider that a previous patient was treated using IMRT technique with 7 fields. In this example, the reference plan 604 for this previous patient would contain information regarding the IMRT technique with 7 fields, field geometries, critical organs information, and objectives that were defined during the optimization for the previous treatment plan (the reference plan 604). When transferring the information from the reference plan for use to determine the new treatment plan 616 (step 204), the processor 54 may be configured to automatically initialize the 7 fields from the reference plan for the new treatment plan 616. In addition, same objectives that were used in the reference plan 604 may be used for the new treatment plan 616. For example, if spinal cord must have less than 20 Gy, and target region must have at least 50 Gy, such objectives may be used for the new patient's treatment plan 616. Also, information regarding structures, such as critical organs or other structures, may be transferred (e.g., automatically) from the reference plan 604 for use to determine the new treatment plan 616. In some embodiments, the processor 54 is configured for performing a deformable image registration between reference image 606 and the new patient image 607 to determine a deformation filed 610, as discussed herein. Also in some embodiments, the dose distribution from the reference plan 604 may be transferred using deformable image registration, as described in more detail below. In such cases, the DVHs may be calculated based on a deformed dose distribution.

Returning to the method 200 of FIG. 2, next, the processor 54 determines a deformed dose distribution 612 (Step 206). In the illustrated embodiments, the deformed dose distribution 612 is determined based on the deformation field 610 that is used to register the reference image 606 with the new patient image 607 (FIG. 6). Thus, if the reference plan 604 was previously selected based on deformable registration technique described above, then the same deformation field 610 that was determined previously may be used. Alternatively, if the reference plan 604 was previously not selected based on deformable registration (e.g., if it was selected based on other criteria), then the processor 54 may determine the deformation field 610 by mapping the reference patient image 606 from the selected reference plan 604 with the new patient image 607. In the illustrated embodiments, the deformed dose distribution 612 is determined by applying the deformation field 610 to deform the reference dose distribution 608 from the selected reference plan 604 (FIG. 6). The reference dose distribution 608 (e.g., 608a, 608b, 608c, 608d) is a dose distribution that was determined previously for the reference patient. In some embodiments, the reference dose distribution represents dose that was previously accomplished. In some cases, the reference dose distribution may contain information about what was accepted previously. For example, a clinical expert has evaluated the effects of a previous dose distribution (e.g., dose in critical organ), and has determined that they are acceptable for the particular clinical situation.

FIGS. 5A-5D show an example to illustrate such concept. FIG. 5A illustrates an image of a region in the new patient 28 in which value 0 represents air outside the patient, 1 represents a healthy tissue, and 2 represents tumorous tissue (target region). FIG. 5B illustrates a reference image of a region in the reference patient that was from the reference plan 604 selected by the processor 54 or user. The resulting deformation field 610 to map the reference image with the new patient image would be a scaling field (e.g., scaling down by a factor of 2 in the vertical direction). FIG. 5C illustrates a reference dose distribution 608 from the reference plan 604 which was previously determined for the reference patient with the reference image 606. In the illustrated example, some parts of the healthy tissue has dose of 1, and other parts of the healthy tissue has dose of 2. Also, as shown in the example, some parts of the target region has dose of 4, and other parts of the target region has dose of 5. FIG. 5D illustrates a deformed dose distribution 612, which is obtained by applying the same deformation field 610 (in the example, it is a scaling field that scales down by a factor of 2 in the vertical direction) to the reference dose distribution 608. As shown in the example, the reference dose distribution 608 in FIG. 5C is scaled down by a factor of 2 in the vertical direction to achieve the deformed dose distribution 612 for the new patient 28. The resulting deformed dose distribution 612 represents an approximation of the dose distribution that may be achievable for the new patient 28. As illustrated in the above example, the resulting deformed dose distribution 612 provides an approximation of doses that may be accomplishable for different tissues in the new patient' 28 having similar respective characteristics as those in the reference patient. In other embodiments, the deformable registration may utilize image of the patient that does not include tumorous tissue. For example, in other embodiments, the value "2" in the above example may represent healthy tissue (i.e., instead of tumorous tissue) with a characteristic that is different from that of the healthy tissue represented by the value "1." Thus, in other embodiments, the resulting deformed dose distribution 612 may include information regarding dose distribution for only healthy tissue. In further embodiments, the resulting deformed dose distribution 612 may include information regarding dose distribution for only unhealthy tissue (e.g., tumorous tissue).

In some cases, if the remaining deformation field indicates that much residual deformation is needed in order to match the new patient image 607, the processor 54 may be configured to perform smoothing function to smooth the deformed dose distribution 612 at the region(s) of interest that requires adjustment. In such cases, the resulting deformed dose distribution 612 would not exactly correspond with the reference dose distribution 608 from the reference plan 604. However, such resulting deformed dose distribution 612 may still provide a good approximation of a desired treatment plan 616 for the new patient 28. Such resulting deformed dose distribution 612 may also provide additional information for the user to determine what could be achieved using the parameters and treatment information from the selected reference plan 604.

In some embodiments, a user interface (e.g., the screen 56) may display graphics that allow a user to see the deformed dose distribution 612. The user interface may also display the deformed dose distribution 612 with the new patient image 607, which allows the user to see how the deformed dose distribution 612 would be applied to different structures in the new patient 28.

After the deformed dose distribution 612 is determined, the processor 54 then performs optimization to determine treatment parameter(s) (Step 208). A treatment parameter may be a leaf sequence, a collimator position, a gantry rotation speed, a gantry position, a couch position, a beam activation signal, a beam deactivation signal, a dose, a dose rate, a beam energy, a beam type, a parameter defining a geometrical configuration of a radiation device, or any other parameter that may be used to define at least a part of a treatment plan. In step 208, the optimization is performed in an attempt to achieve the deformed dose distribution 612, which represents the prescribed dose for the new patient 28. Thus, one objective for the optimization is to find the beam shaping and modulations that minimizes, or at least reduces, the difference between the new dose distribution 614 and the deformed reference dose distribution 612. The new dose distribution 614 may be allowed to deviate from deformed reference dose distribution 612 according to other constraint information available from reference plan 604. For example, lower doses may be allowed in regions that are critical organ(s), and/or more homogeneous dose may be allowed in target region(s).

In some cases, the deformed dose distribution 612 may not be achievable in the new patient 28 due to differences in geometry, such as patient geometry and/or machine geometry. This means that the new dose distribution 614 may be worse in some parts of the new patient 28 compared to the reference patient. However, this could also mean that the new dose distribution 614 in the new patient 28 after optimization may be better than the deformed dose distribution 612. In either case, the deformed dose distribution 612 may be used as an objective to guide the optimization process. However, other objectives (e.g., the objectives used in the optimization for the reference patient) may also be used in the optimization. For example, an objective used in the optimization for the reference patient may be to have less than 20 Gy dose in spinal cord. Such objective may not have been possible to reach with the reference patient. However, with the new patient 28, it may be possible to achieve this objective. Thus, the optimizer (e.g., the processor 54) is configured to attempt to achieve better dose distribution based on such objective even though it may not have been achieved in the reference patient.

Various optimization techniques may be used in step 208. For example, in some embodiments, fluence based optimization may be performed. In other embodiments, direct aperture optimization may be performed. In further embodiments, different techniques may be combined. Direct aperture methods refer to directly modeling the treatment in machine parameters. A subgroup of direct aperture methods is gradient based, and in these cases, the gradients are calculated with respect to machine parameters. Another example of direct aperture method is a simulated annealing optimization. In such cases, a random change is applied to the treatment plan. If the changed treatment plan is better than without the change, the change is applied. On the other hand, if the change makes the plan worse, it is not applied. The quality is evaluated by calculating the dose to both plans and calculating an objective function based on the dose distributions and objectives in the optimization. Techniques for fluence based optimization and direct aperture optimization are known in the art, and will not be described in detail. It should be noted that the method 200 is not limited to the examples of the optimization technique described, and that other optimization techniques known in the art may be used in the method 200 in other embodiments.

In some embodiments, when performing the optimization, the radiation that is desired to be delivered may be modeled by considering fluence. Fluence is the amount of radiation passing through a spatial region, and may be represented by a fluence map. A fluence map is a matrix that covers a spatial region (e.g., a plane). For each point in the plane, the fluence map defines the amount of radiation passing through that element. In such embodiments, the objective of the optimization in step 208 is to determine fluence maps that produce best dose (e.g., a dose that corresponds to the deformed dose distribution 612) in the patient 28 by optimizing the individual components in the fluence maps.

In some cases, the optimization objective may be defined using dose volume histogram (DVH) constraints in patient dose. The DVH indicates the fraction (or absolute amount) of volume that receives at least DVH(x) dose. For example a dose distribution 00000
11111
22211
00000 contains 10 units of dose level 0, 7 units of dose level 1, and 3 units of dose level 2. In this example, such distribution may be represented by a differential dose volume histogram:

| Dose(D) | units with dose D |
|---------|-------------------|
| 0 | 10 |
| 1 | 7 |
| 2 | 3 |
| 3 | 0 |

The corresponding DVH would be:

| Dose(D) | DVH(D) |
|---------|--------|
| 0 | 20 |
| 1 | 10 |
| 2 | 3 |
| 3 | 0 |

In some embodiments, the DVH may be a function, such as that starts from maximum value (100% of units) for 0 dose, and decreases after that to have value of 0 (0 unit) for maximum dose. In such cases, a two dimensional DVH constraint is a constraint that describes which shapes or functions of DVH are preferred. In accordance with some embodiments, during optimization to determine the new treatment plan 616 for the new patient 28, both three dimensional objective(s) and two dimensional DVH objectives are used. For example, a three dimensional objective could be:

| Objective at Z = 1 | Objective at Z = 2 |
|--------------------|--------------------|
| 001100 | 001000 |
| 012210 | 011220 |

| Objective at Z = 1 | Objective at Z = 2 |
|---|---|
| 001210 | 112210 |
| 000000 | 000110 | where regions with 0 can receive 0 dose, regions with 1 can receive 1 Gy dose, and regions with 2 can receive 2Gy dose. In the above example, only two layers (corresponding to Z=1 and Z=2) of the objective for two different respective portions of the patient 28 are shown, but it is understood that a three dimensional objective may include more than two layers, or less than two layers (e.g., one layer) in other examples. In some embodiments, in the three dimensional constraint, a user may specify (e.g., using a user interface) not to put more than a certain dose limit for critical organ (e.g., less than 30 Gy dose to spinal cord), and/or to keep the dose in target region between a prescribed dose range (e.g., between 60 and 70 Gy). The objective is to give the desired dose at the target, while minimizing dose to healthy tissue outside the target. As illustrated in the above example, in a three dimensional objective, certain spatial location, such as x=2 and y=2, may be prescribed to have a certain constraint, such as to receive less than 30 Gy of dose. In some cases, the objective (e.g., that the spine should receive less than 30 Gy dose) can be represented by a DVH objective. The user has defined the spine region and requested that in spine 0% of spine should receive more than 30 Gy dose. With three dimensional objective, the user could define a spatially variant dose objective inside spine, or paint the objective in a patient volume, without explicitly stating what regions are to be considered as one group.

In some embodiments, the optimization process is performed to determine a new treatment plan 616 that involves intensity modulated radiation therapy (IMRT). With IMRT, it is possible to modulate the intensity of individual radiation beams converging on the tumor from multiple angles to shape the 3D dose distribution inside of the patient, thereby delivering desirable doses of radiation to the tumor while avoiding the critical organs at risk. In other embodiments, the treatment plan 616 may not involved IMRT.

Returning to FIG. 2, after the optimization, if the new dose distribution 614 for the new patient 28 is acceptable, the determined treatment parameter(s) may then be accepted as part(s) of the new treatment plan 616 (Step 210). In such cases, the determined treatment parameter(s) from the optimization may be saved in a medium for the actual treatment. In other embodiments, the determined treatment parameter(s) may be saved in a medium for further evaluation. In some cases, if the new dose distribution 614 for the new patient 28 is not acceptable to a user, the user may adjust parameter(s) for the optimization, and re-run the optimization to get new dose distribution 614. For example, the user may change the objective functions, one or more constraints, etc., using the user interface.

In some embodiments, the user interface (e.g., screen 56) may display a graphic that represents the new dose distribution 614, which allows a user to determine whether the new dose distribution 614 is acceptable. For example, in some embodiments, the determined new dose distribution 614 may be displayed next to, or superimposed with, the deformed dose distribution 612, so that the user can see the difference between the two. The region(s) where the new dose distribution 614 is worse than the deformed reference dose distribution 612 may be highlighted to user. Alternatively, or additionally, the determined new dose distribution 614 may be displayed next to the reference dose distribution 608, so that the user can see the difference between the two. The interface may also presents input graphic for allowing the user to accept or reject the determined treatment plan 616.

As illustrated in the above embodiments, using a reference plan 604 for a reference patient for determining a new treatment plan 616 for a new patient 28 is advantageous in that it obviates the need to manually segment the target region and critical organs, thereby making the treatment planning process less time consuming. For example, in some cases in which the target region is composed of organ(s) or parts of organ(s), the target region can be automatically determined without requiring the user to manually determine it. The above described embodiments of the treatment planning process are also advantageous in that they do not require a planner to manually create dose distribution, and/or constraints for optimization, from scratch for the new patient 28. The process can be automated using a processor in some embodiments, and still allow different treatment plans to be customized for different patients. Further, in some cases, the above described treatment planning technique allows three-dimensional objective(s) derived from a previous plan (e.g., for another patient) to be used during the optimization process.

Although the above embodiments have been described with reference to delivering treatment radiation that is in the form of x-rays, in other embodiments, the system and technique described herein may be used for other types of treatment energy. For examples, in other embodiments, the radiation source 20 may be a proton source for delivering protons to treat a patient, or an electron source for delivering electrons. Accordingly, embodiments of the treatment planning technique described herein may be used to determine treatment plan for other types of treatment, such as proton treatment. Also, it should be noted that the term "collimator" is not limited to a device having leaves for blocking radiation, and may refer to a device having one or more jaws or jaw blocks. Thus, a position of a collimator may refer to position of leaves of a collimator, position of collimator jaws, or a global position of the collimator itself relative to some coordinate system (e.g., a position of the collimator relative to a gantry or relative to a radiation machine, etc.).

Computer System Architecture

Figure 7:
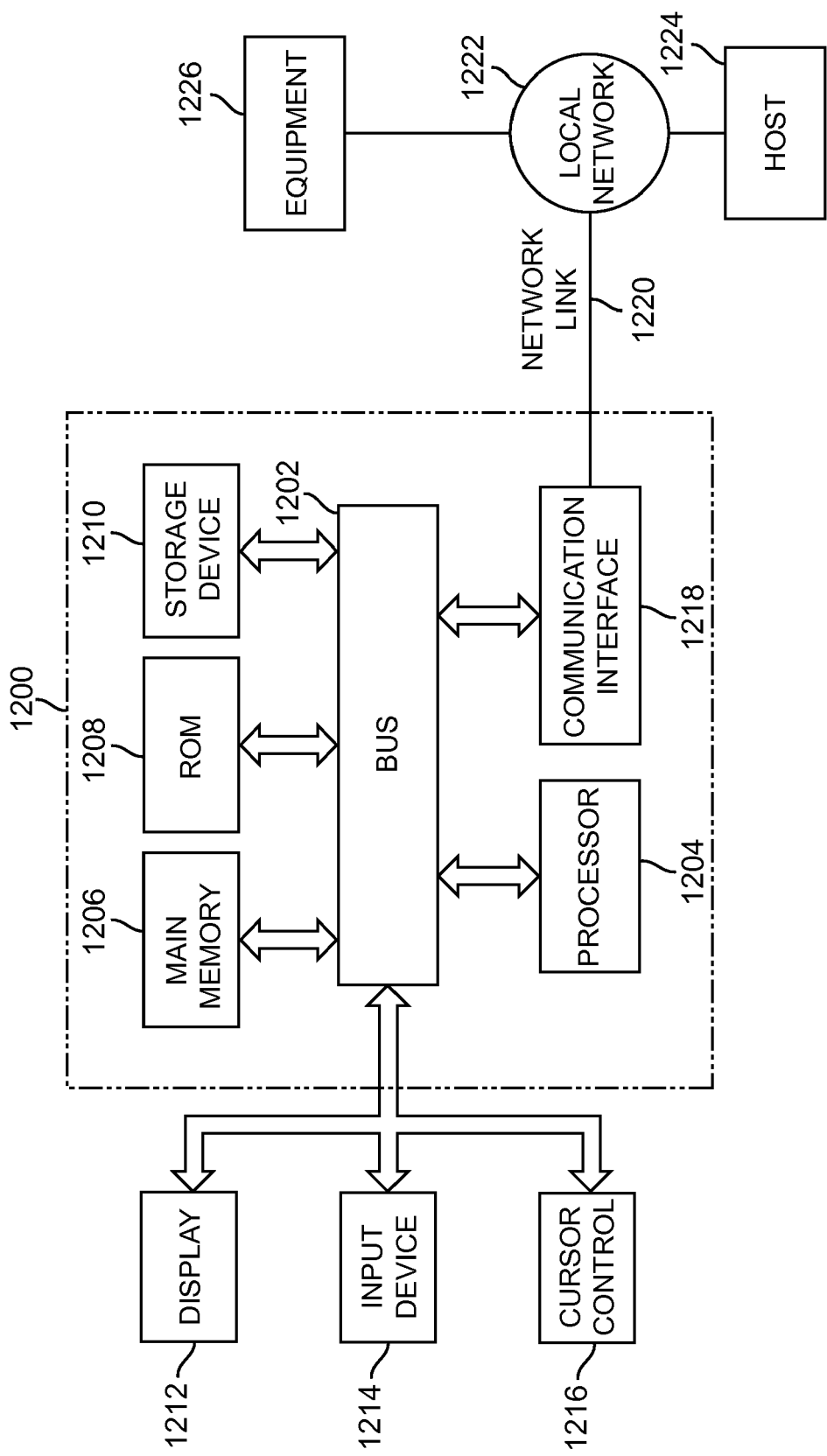
FIG. 7 is a block diagram of a computer system architecture, with which embodiments described herein may be implemented.

FIG. 7 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network (s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. For example, the term "image" as used in this specification needs not be limited to image that is displayed, and may refer to image data that is not displayed for viewing, such as image data that is stored in a medium. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method for determining a radiation treatment plan for a patient, comprising:
    obtaining a reference plan, the reference plan including information regarding a reference region that has a different configuration from that of a region in the patient;
    using the reference plan to determine the treatment plan for the patient, wherein the treatment plan is determined using a processor; and
    storing the treatment plan;
    wherein the reference plan includes data regarding a reference dose distribution, and the act of using the reference plan comprises deforming the reference dose distribution to fit the region in the patient; and
    wherein the reference plan is for a different patient.

2. The method of claim 1, further comprising determining the reference plan, wherein the reference plan is determined based on a case classification.

3. The method of claim 1, further comprising determining the reference plan, wherein the reference plan is determined based on one or a combination of a patient's weight, a patient's age, a patient's height, a patient's sex, an organ to be treated, an organ's size, an organ's shape, a medical condition, and a medical history.

4. The method of claim 1, wherein the reference plan comprises data regarding one or more of a number of fields, a field geometry, a target region, a critical organ, a dose requirement, and a dose limit.

5. The method of claim 1, wherein the act of using the reference plan further comprises evaluating the deformed dose distribution as it applies to the patient.

6. The method of claim 1, wherein the act of deforming the reference dose distribution is performed using a deformable image registration.

7. The method of claim 6, wherein the deformable image registration is for morphing the reference region to the region in the patient.

8. The method of claim 1, wherein the act of using the reference plan comprises performing an optimization using information derived from the reference plan.

9. The method of claim 8, wherein the act of performing the optimization comprises allowing a dose to be more homogeneous in a target region than in a non-target region, and lower in the non-target region than in the target region.

10. The method of claim 8, wherein the optimization is performed to determine a fluence map that represents an amount of radiation passing through a spatial region.

11. The method of claim 8, wherein the optimization is performed to determine a machine parameter, the machine parameter selected from the group consisting of leaf sequence, collimator position, gantry rotation speed, gantry position, couch position, beam activation signal, beam deactivation signal, dose, dose rate, beam energy, beam type, and a parameter defining a geometrical configuration of a radiation device.

12. The method of claim 1, wherein the act of using the reference plan comprises transferring a treatment technique from the reference plan to the treatment plan.

13. The method of claim 1, wherein the act of using the reference plan comprises using an objective function from the reference plan to determine the treatment plan.

14. A method for determining a radiation treatment plan for a patient, comprising:
obtaining a reference plan, the reference plan including information regarding a reference region that has a different configuration from that of a region in the patient;
using the reference plan to determine the treatment plan for the patient, wherein the treatment plan is determined using a processor; and
storing the treatment plan;
wherein the reference plan includes data regarding a reference dose distribution, and the act of using the reference plan further comprises performing an optimization using the reference dose distribution to determine a new dose distribution; and
wherein the reference region is not a part of the patient.

15. The method of claim 14, further comprising visually informing a user a difference between the reference dose distribution and the new dose distribution.

16. A computer product comprising a non-transitory medium for storing a set of instructions, an execution of which causes a process for determining a radiation treatment plan for a patient to be performed, the process comprising:
obtaining a reference plan, the reference plan including information regarding a reference region that has a different configuration from that of a region in the patient; and
using the reference plan to determine the treatment plan for the patient;
wherein the reference plan includes data regarding a reference dose distribution, and the act of using the reference plan comprises deforming the reference dose distribution to fit the region in the patient; and
wherein the reference region belongs to a different patient.

17. The computer product of claim 16, wherein the process further comprises determining the reference plan, wherein the reference plan is determined based on one or a combination of a patient's weight, a patient's age, a patient's height, a patient's sex, an organ to be treated, an organ's size, an organ's shape, a medical condition, and a medical history.

18. The computer product of claim 16, wherein the reference plan comprises data regarding one or more of a number of fields, a field geometry, a target region, a critical organ, a dose requirement, and a dose limit.

19. The computer product of claim 16, wherein the act of using the reference plan further comprises evaluating the deformed dose distribution as it applies to the patient.

20. The computer product of claim 16, wherein the act of using the reference plan further comprises performing an optimization using the deformed reference dose distribution to determine a new dose distribution.

21. The computer product of claim 20, wherein the process further comprises visually informing a user of a difference between the deformed reference dose distribution and the new dose distribution.

22. The computer product of claim 16, wherein the act of using the reference plan comprises transferring a treatment technique from the reference plan to the treatment plan.

23. A system for determining a radiation treatment plan for a patient, comprising:
means for obtaining a reference plan, the reference plan including information regarding a reference region that has a different configuration from that of a region in the patient; and
means for using the reference plan to determine the treatment plan for the patient, wherein the means for using the reference plan comprises a processor;
wherein the reference plan includes data regarding a reference dose distribution, and the means for using the reference plan is configured for deforming the reference dose distribution to fit the region in the patient;
wherein the reference region belongs to a different patient.

24. The system of claim 23, wherein the means for obtaining the reference plan is configured to obtain the reference plan based on one or a combination of a patient's weight, a patient's age, a patient's height, a patient's sex, an organ to be treated, an organ's size, an organ's shape, a medical condition, and a medical history.

25. The system of claim 23, wherein the reference plan comprises data regarding one or more of a number of fields, a field geometry, a target region, a critical organ, a dose requirement, and a dose limit.

26. The system of claim 23, wherein the processor is configured for transferring a treatment technique from the reference plan to the treatment plan.

27. A method for use in a treatment planning process, comprising:
obtaining a reference plan that includes information regarding a reference region;
determining a deformation field that registers the reference region in the reference plan with a region for a patient using a processor;
determining a result of using the reference plan as it applies for the patient; and storing the result;
wherein the reference region is not a part of the patient.

28. The method of claim 27, further comprising determining the reference plan, wherein the reference plan is determined based on one or a combination of a patient's weight, a patient's age, a patient's height, a patient's sex, an organ to be treated, an organ's size, an organ's shape, and a medical condition.

29. A method for use in a treatment planning process, comprising:
   obtaining a reference plan that includes information regarding a reference region;
   determining a deformation field that registers the reference region in the reference plan with a region for a patient using a processor;
   determining a result of using the reference plan as it applies for the patient; and
   storing the result;
   wherein the act of determining the result comprises removing rotation component, scaling component, and translation component from the deformation field to determine a remaining deformation field, the remaining deformation field being the result.

30. The method of claim 29, wherein the act of determining the result comprises determining a dose distribution based on the deformation field.

31. A method for use in a treatment planning process, comprising:
   obtaining a reference plan that includes information regarding a reference region;
   determining a deformation field that registers the reference region in the reference plan with a region for a patient using a processor;
   determining a result of using the reference plan as it applies for the patient;
   storing the result; and
   determining a divergence component and a curl component of the deformation field.

32. A computer product includes a non-transitory medium for storing a set of instructions, an execution of which causes a process to be performed, the process comprising:
   obtaining a reference plan that includes information regarding a reference region;
   determining a deformation field that registers the reference region in the reference plan with a region for a patient; and
   determining a result of using the reference plan as it applies for the patient;
   wherein the reference region is not a part of the patient.

33. The computer product of claim 32, wherein the act of determining the result comprises determining a dose distribution based on the deformation field.

34. A computer product includes a non-transitory medium for storing a set of instructions, an execution of which causes a process to be performed, the process comprising:
   obtaining a reference plan that includes information regarding a reference region;
   determining a deformation field that registers the reference region in the reference plan with a region for a patient; and
   determining a result of using the reference plan as it applies for the patient;
   wherein the act of determining the result comprises removing rotation component, scaling component, and translation component from the deformation field to determine a remaining deformation field, the remaining deformation field being the result.

35. A system for use in a treatment planning process, comprising:
   means for obtaining a reference plan that includes information regarding a reference region;
   means for determining a deformation field that registers the reference region in the reference plan with a region for a patient, wherein the means for determining the deformation field comprises a processor; and
   means for determining a result of using the reference plan as it applies for the patient
   wherein the reference region is not a part of the patient.

* * * * *